(12) United States Patent
Hirano et al.

(10) Patent No.: US 9,416,403 B2
(45) Date of Patent: Aug. 16, 2016

(54) METHOD OF DETECTING TARGET NUCLEIC ACID

(71) Applicant: Toray Industries, Inc., Tokyo (JP)

(72) Inventors: Taisuke Hirano, Kamakura (JP); Fumio Nakamura, Kamakura (JP); Yoji Ueda, Kamakura (JP); Kenzo Fujimoto, Nomi (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/423,493

(22) PCT Filed: Aug. 29, 2013

(86) PCT No.: PCT/JP2013/073083
§ 371 (c)(1),
(2) Date: Feb. 24, 2015

(87) PCT Pub. No.: WO2014/034753
PCT Pub. Date: Mar. 6, 2014

(65) Prior Publication Data
US 2015/0240296 A1  Aug. 27, 2015

(30) Foreign Application Priority Data

Aug. 31, 2012  (JP) ................................. 2012-191226

(51) Int. Cl.
*C12Q 1/68* (2006.01)
(52) U.S. Cl.
CPC ............ *C12Q 1/6825* (2013.01); *C12Q 1/6834* (2013.01)
(58) Field of Classification Search
None
See application file for complete search history.

(56) References Cited

U.S. PATENT DOCUMENTS

| | | | |
|---|---|---|---|
| 4,486,539 A | 12/1984 | Ranki et al. | |
| 5,705,610 A | 1/1998 | Zuckermann et al. | |
| 6,242,266 B1 | 6/2001 | Schleifer et al. | |
| 2003/0143132 A1 | 7/2003 | Cerrina et al. | |
| 2004/0191806 A1* | 9/2004 | Huan ................ | C12Q 1/6827 506/9 |
| 2007/0207465 A1* | 9/2007 | Kayyem ............ | C12Q 1/6825 435/6.11 |
| 2010/0274000 A1 | 10/2010 | Fujimoto et al. | |
| 2013/0177918 A1 | 7/2013 | Terasaki et al. | |

FOREIGN PATENT DOCUMENTS

| EP | 2 216 338 A1 | 8/2010 |
|---|---|---|
| JP | 58-501703 A | 10/1983 |
| JP | 07-075600 A | 3/1995 |
| JP | 10-503841 A | 4/1998 |
| JP | 2001-069997 A | 3/2001 |
| JP | 3922454 B2 | 5/2007 |
| JP | 2011-036150 A | 2/2011 |
| JP | 2012-509063 A | 4/2012 |
| WO | 2004/020675 | 3/2004 |
| WO | 2009/066447 A1 | 5/2009 |
| WO | 2012/033190 | 3/2012 |
| WO | 2013/140890 A1 | 9/2013 |

OTHER PUBLICATIONS

Yoshimura, Y. et al., "Interstrand Photocrosslinking for Sensitive Assays in the Diagnostic Detection of DNA Sequences," *Nen Symposium on Photochemistry*, 2008, p. 49, IC07 along with an English abstract (2 sheets).

Nikolaus Blin et al., "A general method for isolation of high molecular weight DNA from eukaryotes," Nucleic Acids Res., vol. 3, No. 9, 1976, pp. 2303-2308 (Abstract).

Jennifer Favaloro et al., "Transcription maps of polyoma virus-specific RNA: Analysis by two-dimensional nuclease S1 gel mapping," Methods in Enzymology, vol. 65, 1980, pp. 718-749 (Abstract).

Sinikka Parkkinen et al., "Detection of Human Papillomavirus DNA by the Nucleic Acid Sandwich Hybridization Method From Cervical Scraping," Journal of Medical Virology, vol. 20, No. 3, 1986, pp. 279-288 (Abstract).

Kenzo Fujimoto et al., "Photoinduced DNA end capping via$N^3$-methyl-5-cyanovinyl-2'-deoxyuridine," Chemical Communications, 2005, pp. 3177-3179 (Abstract).

Shinzi Ogasawara et al., "High selectivity detection of point mutation by DNA photochemical cross-linking," Nucleic Acids Symposium Series, No. 50, 2006, pp. 173-174.

T. Ami et al., "Sequence specific interstrand photocrosslinking for effective SNP typing," Org. Biomol. Chem., vol. 5, No. 16, 2007, pp. 2583-2586 (Abstract).

Yoshinaga Yoshimura et al., "Ultrafast Reversible Photo-Cross-Linking Reaction: Toward in Situ DNA Manipulation," Org. Lett., vol. 10, No. 15, 2008, pp. 3227-3230 (AbstractO.

Akio Kobori et al., "Synthesis and Photoinduced Cross-linking Reactions of 4,5',8-Trimethylpsoralen-incorporated Oligodeoxyribonucleotide," Chemistry Letters, vol. 38, No. 3, 2009, pp. 272-273 (Abstract).

Supplementary European Search Report dated Mar. 4, 2016 of corresponding European Application No. 13832897.6.

\* cited by examiner

*Primary Examiner* — James Martinell
(74) *Attorney, Agent, or Firm* — DLA Piper LLP (US)

(57) ABSTRACT

A method of detecting a target nucleic acid by sandwich hybridization using a detection probe that hybridizes with the target nucleic acid, and a capture probe immobilized on a support wherein at least one nucleic acid base in the nucleic acid molecule(s) of the detection probe and/or capture probe with a photoreactive group includes irradiating, with light, a complex formed by hybridization between the target nucleic acid and the detection probe and/or capture probe to allow formation of a covalent bond(s) between the photoreactive group(s) and a nucleic acid base(s) in the target nucleic acid.

2 Claims, No Drawings

```
                        SEQUENCE LISTING

<160> NUMBER OF SEQ ID NOS: 28

<210> SEQ ID NO 1
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaaaaataaa ctgtaaatca tattcctccc catgtcgtag gtactcctta aagttagtat      60
ttttatatgt agtttctgaa gtagatatgg cagcacataa tgacatattt gtactgcgtg     120
tagtatcaac aacagtaaca aa                                              142

<210> SEQ ID NO 2
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
tcagaggtaa ccatagaacc actaggtgta ggaaaataat ttgaactggc taaatttgca      60
gtagacccag agcctttaat gtataaatcg tctggtacat tttcaccaac agtaccagcc    120
ctattaaata aatgtctaac                                                140

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end and 3'-end biotin-labeling

<400> SEQUENCE: 3
tttgttactg ttgttgatac tac                                              23
```

```
<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end and 3'-end biotin-labeling

<400> SEQUENCE: 4
gaatatgatt tacagtttat ttttc                                           25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end and 3'-end biotin-labeling

<400> SEQUENCE: 5
acatttattt aatagggctg gtact                                           25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end and 3'-end biotin-labeling

<400> SEQUENCE: 6
ctagtggttc tatggttacc tctga                                           25

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end and 3'-end biotin-labeling

<400> SEQUENCE: 7
acatgtcaca cataaggtta aaacactatc aaatactcca                           40

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end and 3'-end biotin-labeling

<400> SEQUENCE: 8
cagtcatttt cagcaggcct tataataaaa ataatgaaaa                           40

<210> SEQ ID NO 9
<211> LENGTH: 40
<212> TYPE: DNA
```

-continued

```
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end and 3'-end biotin-labeling

<400> SEQUENCE: 9
gatcatattc gtccacaaaa tgattctgaa ttagctgtat                            40

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end and 3'-end biotin-labeling

<400> SEQUENCE: 10
gaatggtcct gcaccagtaa tatgcatatt aaaacaagat                            40

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end amino group

<400> SEQUENCE: 11
gtcattatgt gctgccatat ctacttcaga                                       30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end biotin-labeling

<400> SEQUENCE: 12
gtcattatgt gctgccatat ctacttcaga                                       30

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end amino group

<400> SEQUENCE: 13
tttttgattt atacattaaa ggctctgggt ctact                                 35

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
```

-continued

```
<220> FEATURE:
<223> OTHER INFORMATION: 5'-end amino group

<400> SEQUENCE: 14
agttggagct ggtggcgtag g                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end amino group

<400> SEQUENCE: 15
agttggagct agtggcgtag g                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end amino group

<400> SEQUENCE: 16
agttggagct cgtggcgtag g                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end amino group

<400> SEQUENCE: 17
agttggagct tgtggcgtag g                                              21

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end and 3'-end biotin-labeling
<220> FEATURE:
<221> NAME/KEY: modified_base
<222> LOCATION: (23)..(23)
<223> OTHER INFORMATION: 3-cyanovinylcarbazole nucleotide

<400> SEQUENCE: 18
tttgttactg ttgttgatac tan                                            23

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
```

```
<220> FEATURE:
<223> OTHER INFORMATION: 5'-end and 3'-end biotin-labeling
<220> FEATURE:
<221> NAME/KEY: modified_base
<222> LOCATION: (3)..(3)
<223> OTHER INFORMATION: 3-cyanovinylcarbazole nucleotide

<400> SEQUENCE: 19
gantatgatt tacagtttat ttttc                                          25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end and 3'-end biotin-labeling
<220> FEATURE:
<221> NAME/KEY: modified_base
<222> LOCATION: (13)..(13)
<223> OTHER INFORMATION: 3-cyanovinylcarbazole nucleotide

<400> SEQUENCE: 20
acatttattt aanagggctg gtact                                          25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end and 3'-end biotin-labeling
<220> FEATURE:
<221> NAME/KEY: modified_base
<222> LOCATION: (13)..(13)
<223> OTHER INFORMATION: 3-cyanovinylcarbazole nucleotide

<400> SEQUENCE: 21
ctagtggttc tanggttacc tctga                                          25

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end and 3'-end biotin-labeling
<220> FEATURE:
<221> NAME/KEY: modified_base
<222> LOCATION: (22)..(22)
<223> OTHER INFORMATION: 3-cyanovinylcarbazole nucleotide

<400> SEQUENCE: 22
acatgtcaca cataaggtta anacactatc aaatactcca                          40

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end and 3'-end biotin-labeling
<220> FEATURE:
```

```
<221> NAME/KEY: modified_base
<222> LOCATION: (23)..(23)
<223> OTHER INFORMATION: 3-cyanovinylcarbazole nucleotide

<400> SEQUENCE: 23
cagtcatttt cagcaggcct tanaataaaa ataatgaaaa                              40

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end and 3'-end biotin-labeling
<220> FEATURE:
<221> NAME/KEY: modified_base
<222> LOCATION: (16)..(16)
<223> OTHER INFORMATION: 3-cyanovinylcarbazole nucleotide

<400> SEQUENCE: 24
gatcatattc gtccanaaaa tgattctgaa ttagctgtat                              40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end and 3'-end biotin-labeling
<220> FEATURE:
<221> NAME/KEY: modified_base
<222> LOCATION: (21)..(21)
<223> OTHER INFORMATION: 3-cyanovinylcarbazole nucleotide

<400> SEQUENCE: 25
gaatggtcct gcaccagtaa natgcatatt aaaacaagat                              40

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end biotin-labeling
<220> FEATURE:
<221> NAME/KEY: modified_base
<222> LOCATION: (18)..(18)
<223> OTHER INFORMATION: 3-cyanovinylcarbazole nucleotide

<400> SEQUENCE: 26
gtcattatgt gctgccanat ctacttcaga                                        30

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic
      PNA probe

<400> SEQUENCE: 27
tgtgctgcca tatcta                                                       16
```

```
<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-end amino group
<220> FEATURE:
<221> NAME/KEY: modified_base
<222> LOCATION: (19)..(19)
<223> OTHER INFORMATION: 3-cyanovinylcarbazole nucleotide

<400> SEQUENCE: 28
tttttgattt atacattana ggctctgggt ctact                              35
```

METHOD OF DETECTING TARGET NUCLEIC ACID

TECHNICAL FIELD

This disclosure relates to a method of detecting a target nucleic acid by sandwich hybridization.

BACKGROUND

Research by genetic information analysis of various organisms has begun, and information on a number of genes including those of humans and their base sequences, and on the proteins encoded by the gene sequences and sugar chains secondarily produced from these proteins, is being rapidly clarified. Functions of polymers such as genes, proteins and sugar chains whose sequences were clarified can be investigated by various methods. In terms of nucleic acids, major examples of the methods include Northern blotting and Southern blotting, which can be used for investigation of various genes in relation to expression of their biological functions by utilization of various nucleic acid-nucleic acid complementarities. In terms of proteins, representative examples of the methods include Western blotting, which can be used to investigate functions and expression of proteins by utilization of protein-protein reactions.

A known example of the nucleic acid detection method is sandwich hybridization. In sandwich hybridization, a capture probe immobilized on a filter is used. The capture probe is complementary to a first portion of the target nucleic acid. In one stage, the capture probe bound to the filter is exposed to a sample to be investigated for the target nucleic acid sequence, and then exposed to a labeled detection probe complementary to a second portion of the target nucleic acid. The second portion is different from the portion in the target which is complementary to the first probe (i.e., the portions do not overlap with each other) (U.S. Pat. No. 4,486,539, JP 7-75600 A and Sinikka Parkkinen et al., Journal of Medical Virology 20: 279-288 (1986)). That method eliminates the labor required for immobilization of the sample on the filter, and enables selection of a first probe applicable to the support.

Conventionally, detection of a target nucleic acid by sandwich hybridization on a support having a capture probe immobilized thereon required an excessive amount of a detection probe relative to the amount of the target nucleic acid. For example, according to JP 2001-69997 A, 250,000 equivalents of the detection probe with respect to the amount of the target nucleic acid is required. However, use of an excessive amount of the detection probe causes cross-hybridization of the excessive detection probe with capture probes to capture other target nucleic acids (non-specific adsorption), resulting in a low detection sensitivity (S/N ratio), which is problematic.

It could therefore be helpful to provide a method of detecting a target nucleic acid, which enables highly sensitive detection of a target nucleic acid without lowering the detection sensitivity (S/N ratio) even by use of a reduced amount of a detection probe.

SUMMARY

We discovered that, in sandwich hybridization, by light irradiation of a complex formed by hybridization between the target nucleic acid and the detection probe and/or capture probe to allow formation of a covalent bond(s) between a photoreactive group(s) with which a nucleic acid base(s) in the detection probe and/or capture probe was/were substituted and a nucleic acid base(s) in the target nucleic acid, the target nucleic acid can be highly sensitively detected without use of an excessive amount of the detection probe.

We thus provide:

(1) A method of detecting a target nucleic acid by sandwich hybridization using a detection probe that hybridizes with the target nucleic acid, and a capture probe immobilized on a support,
wherein at least one nucleic acid base in the nucleic acid molecule(s) of the detection probe and/or capture probe is substituted with a photoreactive group,
the method comprising the step of irradiating, with light, a complex formed by hybridization between the target nucleic acid and the detection probe and/or capture probe to allow formation of a covalent bond(s) between the photoreactive group(s) and a nucleic acid base(s) in the target nucleic acid.

(2) The detection method according to (1), wherein at least one nucleic acid base in the nucleic acid molecule of the detection probe is substituted with the photoreactive group.

(3) The detection method according to (2), wherein at least one nucleic acid base in the nucleic acid molecule of the capture probe is substituted with the photoreactive group.

(4) The detection method according to any one of (1) to (3), wherein the photoreactive group is at least one selected from the group consisting of 3-cyanovinylcarbazole, p-carbamoylvinylphenol, 4,5',8-trimethylpsoralen, and $N^3$-methyl-5-cyanovinyluracil.

The amount of the detection probe to be used can be reduced and, therefore, cross-hybridization with the capture probe (non-specific adsorption) can be suppressed. As a result, the detection sensitivity (S/N ratio) can be increased so that a small amount of a target nucleic acid can be detected with high sensitivity.

DETAILED DESCRIPTION

Examples of the target nucleic acid to be subjected to the detection method include, but are not limited to, genes of pathogenic bacteria and viruses, causative genes for hereditary diseases, and parts of such genes. Examples of samples containing such target nucleic acids include, but are not limited to, body fluids such as blood, serum, plasma, urine, stool, spinal fluid, saliva, swab, and various tissue fluids; various tissues; paraffin-embedded samples (FFPEs) and sections thereof; and various foods and beverages, and dilutions thereof. The target nucleic acid to be used as a test substance may be a sample nucleic acid extracted from blood or cells by a conventional method, and DNA or RNA extracted from a sample may be used. Examples of the DNA which may be used include, but are not limited to, chromosomal DNAs; viral DNAs; DNAs of bacteria, molds, and the like; cDNAs produced by reverse transcription of RNAs; and partial fragments thereof. Examples of the RNA which may be used include, but are not limited to, messenger RNAs, ribosomal RNAs, small RNAs, and partial fragments thereof. A chemically synthesized DNA, RNA or the like may also be used as the target nucleic acid.

The sample nucleic acid sometimes contains a nucleic acid component other than the target nucleic acid to be measured (non-target nucleic acid). Such a non-target nucleic acid may be removed in consideration of its properties different from those of the target nucleic acid, or may be used as the test substance without removal.

The target nucleic acid may be one prepared by amplification by a nucleic acid amplification method such as PCR using the target nucleic acid as a template. In such a case, the measurement sensitivity can be largely increased. When a nucleic acid amplification product is used as the target nucleic acid, the amplified nucleic acid can be labeled by performing the amplification in the presence of nucleoside triphosphate labeled with a fluorescent substance or the like.

The method can be used to detect the presence or absence of a target nucleic acid, genotype of a virus, species and strain of a bacterium, species and strain of a fungus, or the like is identified; detect SNPs (single nucleotide polymorphisms); detect a messenger RNA; detect an miRNA; CGH; detect a copy number change or deletion/duplication/fusion of a genomic DNA sequence; or detect deletion/duplication/fusion of a transcription product. The method can also be applied to quantification of a target nucleic acid by measurement of the signal intensity of a detection probe. Since quantification of a target nucleic acid is inevitably accompanied by detection of the target nucleic acid, the "detection method" also includes when quantification is carried out.

To the method, the target nucleic acid itself may be applied, or a fragmentation product of the target nucleic acid may be applied. The length of the target nucleic acid is not limited as long as hybridization between the capture probe and the detection probe is possible and, when the target nucleic acid is long (when the length is not less than 1500 bases, especially not less than 4000 bases), it is preferred to apply a fragmentation product having an appropriate length(s) prepared by fragmentation treatment as described later. Selection of a specific nucleic acid fragment(s) from the produced nucleic acid fragments is not necessary, and the fragmentation product can be subjected as it is to the method. By this, the detection sensitivity can be increased.

Examples of the method of cleaving the target nucleic acid for the fragmentation include a method in which ultrasonic irradiation is carried out to perform the cleavage, a method in which an enzyme is used to perform the cleavage, a method in which a restriction enzyme is used to perform the cleavage, a method in which a nebulizer is used, and a method in which an acid or alkali is used to perform the cleavage. In the method in which ultrasonication is carried out to perform the cleavage, the output intensity and the irradiation time for the ultrasonication of the target nucleic acid may be controlled such that fragments having a desired length(s) can be obtained.

Examples of the support that may be used include slide glasses, membranes, and beads. Examples of the material of the support include, but are not limited to, inorganic materials such as glass, ceramic and silicon; and polymers such as polyethylene terephthalate, cellulose acetate, polycarbonate, polystyrene, polymethylmethacrylate, and silicone rubber. By using a microarray in which a plurality of capture probes are immobilized on a support, a plurality of types of target nucleic acids can be detected at once.

The method of detecting a target nucleic acid can be preferably applied to sandwich hybridization. Sandwich hybridization uses a capture probe immobilized on a support, and a detection probe. The capture probe and the detection probe usually have base sequences complementary to different portions of the target nucleic acid, and are capable of selectively binding to the target nucleic acid by hybridization. The target nucleic acid hybridizes with the detection probe and/or capture probe to form a complex. By detecting (measuring) a labeling substance bound to the detection probe in the complex, the target nucleic acid can be detected.

Examples of the capture probe that may be used include nucleic acid derivatives such as DNA, RNA, PNA (Peptide Nucleic Acid), and LNA (Locked Nucleic Acid). In a nucleic acid, the derivative herein means a chemically modified derivative such as a derivative labeled with a fluorophore or the like, or a derivative containing a modified nucleotide (for example, a nucleotide having a halogen or a group such as alkyl including methyl; alkoxy including methoxy; thio; carboxymethyl or the like; or a nucleotide that underwent reconstruction of the base, saturation of a double bond, deamination, replacement of an oxygen molecule with a sulfur molecule or the like).

Since a single-stranded nucleic acid having a specific base sequence selectively binds to a single-stranded nucleic acid having the base sequence complementary to the specific base sequence or a part thereof by hybridization, the single-stranded nucleic acid having the specific base sequence corresponds to the capture probe. The capture probe may be one commercially available, or may be obtained from living cells or the like. An especially preferred capture probe is a nucleic acid. Among the nucleic acids, those having lengths of up to 200 bases, which are called oligonucleic acids, can be easily artificially synthesized using a synthesizer.

The capture probe is not limited as long as the probe contains a sequence complementary to the target nucleic acid sequence, and any region may be selected therefor. The sequence preferably does not overlap with the sequence of the detection probe described below. A plurality of types of capture probes that hybridize with different regions of the target nucleic acid may also be used.

When the target nucleic acid is a double-stranded DNA or double-stranded RNA, a sequence complementary to either one of the sense strand and the antisense strand may be selected as the capture probe. In such cases, the sequence of the detection probe described below and the sequence of the capture probe are preferably sequences selected from the same strand.

When different target nucleic acids contained in a sample nucleic acid is to be distinctively detected, for example, when the type of a virus with which a patient is infected is to be distinctively detected, it is preferred to select a sequence region having high specificity in the nucleic sequences that may be contained in the sample nucleic acid. This means that, among all sequences contained in the sample nucleic acid, there is no sequence, other than the sequence of the corresponding region, having high homology to the sequence selected as the capture probe.

At least one nucleic acid base in the nucleic acid molecule of either one of the detection probe and the capture probe is substituted with a photoreactive group, or at least one nucleic acid base in each of the nucleic acid molecules of both the detection probe and the capture probe is substituted with a photoreactive group.

The photoreactive group herein is an organic group (photoreactive site) whose reactivity in organic synthesis reaction is activated by irradiation with light having a specific wavelength. After substitution of the nucleic acid base in the probe with the photoreactive group, the probe is capable of hybridizing with the target nucleic acid to form a complex, similarly to the probe before the substitution. By subjecting the complex formed by hybridization between the capture probe and/or detection probe in which a nucleic acid base(s) is/are substituted with the photoreactive group(s) and the target nucleic acid to irradiation with light having a wavelength capable of activating the photoreactive site(s) of the photoreactive group(s), the photoreactive site(s) is/are activated, and a covalent bond(s) is/are formed between the photoreactive group(s) and a nucleic acid base(s) in the target nucleic acid.

Examples of such a photoreactive group include 3-cyanovinylcarbazole and derivatives thereof (WO 2009/066447 (EP2216338, US 2010-274000 A), Yoshinaga Yoshimura et al., Organic Letters 10: 3227-3230 (2008)), p-carbamoylvinylphenol (Takehiro Ami et al., Organic & Biomolecular Chemistry 5: 2583-2586 (2007)), 4,5',8-trimethylpsoralen (Akio Kobori et al., Chemistry Letters 38: 272-273(2009)), and $N^3$-methyl-5-cyanovinyluracil (Kenzo Fujimoto et al., Chemical Communications: 3177-3179 (2005)). The subject matter of the above-identified literature is herein incorporated by reference. Among these, 3-cyanovinylcarbazole and derivatives thereof (WO 2009/066447) are preferred, and 3-cyanovinylcarbazole is especially preferred.

The 3-cyanovinylcarbazole and derivatives thereof are groups represented by Formula (I) below, as described in WO 2009/066447:

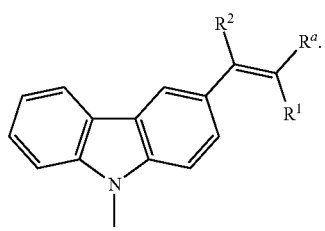

(I)

In Formula (I), $R^a$ represents cyano, amide, carboxyl, $C_2$-$C_7$ alkoxycarbonyl, or hydrogen; and $R^1$ and $R^2$ each independently represent cyano, amide, carboxyl, $C_2$-$C_7$ alkoxycarbonyl, or hydrogen. Formula (I) represents 3-cyanovinylcarbazole in the case where $R^a$ is cyano, and each of $R^1$ and $R^2$ is hydrogen. When 3-cyanovinylcarbazole or a derivative thereof is used as the photoreactive group, the capture probe and/or detection probe is/are preferably designed such that a purine base is located in the 5'-side of, and adjacent to, this base.

p-Carbamoylvinylphenol is the group represented by Formula (II) below:

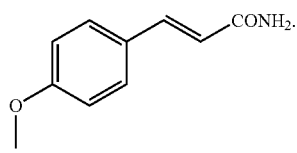

(II)

4,5',8-Trimethylpsoralen is the group represented by Formula (III) below:

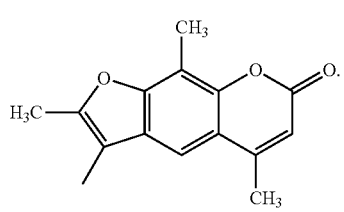

(III)

$N^3$-methyl-5-cyanovinyluracil is the group represented by Formula (IV) below:

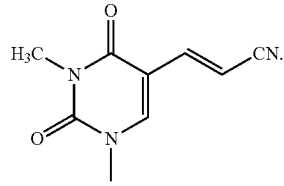

(IV)

Each of these photoreactive groups replaces the whole base in a nucleotide constituting the nucleic acid, and the uncombined hand in each of the photoreactive groups represented by Formulae (I) to (IV) directly binds to the sugar moiety of the nucleotide. For example, 3-cyanovinylcarbazole, represented by Formula (I) (in the case where $R^a$ is cyano, and each of $R^1$ and $R^2$ is hydrogen), binds to a deoxyribose as follows. Each of the other photoreactive groups similarly binds to the sugar.

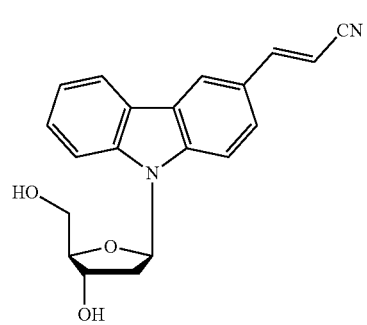

(V)

The photoreactive groups described above, and the binding products between each photoreactive group and a sugar such as deoxyribose can be produced by known methods described in the respective literatures mentioned above. These known methods are ordinary synthesis methods that are in accordance with common knowledge of organic chemical synthesis.

For example, according to Examples of WO 2009/066447, the 3-cyanovinylcarbazole group in Formula (V) is produced by heating 3-iodocarbazole (3.52 mmol) and acrylonitrile (7.04 mmol) in dioxane to reflux in the presence of triphenylphosphine (0.53 μmol), palladium acetate (0.18 μmol), and triethylamine (4.23 mmol) at 75° C. for 11.5 hours. In those Examples, the binding between 3-cyanovinylcarbazole and deoxyribose is achieved by stirring 3-cyanovinylcarbazole (1.20 mmol) and Hoffer's chlorosugar (prepared by replacing the hydroxyl group at 1-position of deoxyribose with chlorine, and the hydroxyl groups at 3-position and 6-position of the deoxyribose with a p-toluoyloxy group) (1.24 mmol) in acetonitrile in the presence of KOH (3.87 mmol) and TDA-1 (34 μmol) at room temperature for 20 minutes, and then adding NaOMe (1.2 mmol) in methanol to the resulting mixture, followed by stirring the resulting mixture at room temperature for 3.5 hours to deprotect the hydroxyl groups at 3-position and 6-position of the deoxyribose. According to the method described in Takehiro Ami et al., Organic & Biomolecular Chemistry 5: 2583-2586 (2007), the binding product between p-carbamoylvinylphenol and deoxyribose is similarly produced by reacting p-iodophenol with Hoffer's chlorosugar to bind them together and then reacting the resulting product with methyl methacrylate.

According to the method described in Akio Kobori et al., Chemistry Letters 38: 272-273 (2009), the binding product between 4,5',8-trimethylpsoralen and deoxyribose is similarly produced by reacting 3-iodo-4,5',8-trimethylpsoralen with Hoffer's chlorosugar. According to the method described in Kenzo Fujimoto et al., Chemical Communications: 3177-3179 (2005), the binding product between $N^3$-methyl-5-cyanovinyluracil and deoxyribose is similarly produced by reacting 2-iodo-$N^3$-methyluridine with acrylonitrile. Also, when a sugar other than deoxyribose (e.g., ribose) is used, a binding product between the photoreactive group and the sugar can be similarly obtained.

After obtaining the binding product between the photoreactive group and the sugar, a nucleic acid containing the binding product can be easily produced by the phosphoramidite method, which is an ordinary method. For example, in Examples of WO 2009/066447, the binding product between 3-cyanovinylcarbazole and deoxyribose (0.29 mmol) represented by Formula (V) described above is reacted with 4,4-dimethoxytrityl chloride (0.35 mmol) and 4-(dimethylamino) pyridine in pyridine at room temperature for 18 hours to protect the hydroxy group at 6-position of the deoxyribose, and the resulting product (0.17 mmol) is stirred with 2-cyanoethyl-N,N,N',N'-tetraisopropylphosphoramidite (0.17 mmol) in acetonitrile at room temperature for 1 hour, to produce a desired phosphoramidite-modified product. The binding products between each of the other photoreactive groups and deoxyribose can be similarly modified with phosphoramidite. Since modification with phosphoramidite is an ordinary method, and reagents therefor are commercially available, the modification can be easily carried out.

After obtaining the phosphoramidite-modified binding product between the photoreactive group and the sugar, a nucleic acid having a desired base sequence can be synthesized using a commercially available oligonucleotide synthesizer.

Nucleic acids having a photoreactive group per se are well known and used as reagents for inhibiting expression of a desired gene or the like, and synthesis of a nucleic acid containing a photoreactive group and having a desired base sequence is available as a commercial service. By requesting synthesis of a nucleic acid having a desired base sequence and containing a photoreactive group(s) introduced at a desired position(s) to a company providing this commercial service, the nucleic acid can be obtained.

Specific examples of the detection probe that may be used include nucleic acid derivatives such as DNA, RNA, PNA, and LNA. In a nucleic acid, the derivative herein means a chemically modified derivative such as a derivative labeled with a fluorophore or the like, or a derivative containing a modified nucleotide (for example, a nucleotide having a halogen or a group such as alkyl including methyl; alkoxy including methoxy; thio; carboxymethyl or the like; or a nucleotide that underwent reconstruction of the base, saturation of a double bond, deamination, replacement of an oxygen molecule with a sulfur molecule or the like).

Since a single-stranded nucleic acid having a specific base sequence selectively binds to a single-stranded nucleic acid having the base sequence complementary to the specific base sequence or a part thereof by hybridization, the single-stranded nucleic acid having the specific base sequence corresponds to the detection probe. The detection probe may be one commercially available, or may be obtained from living cells or the like. An especially preferred detection probe is a nucleic acid. Among the nucleic acids, those having lengths of up to 200 bases, which are called oligonucleic acids, can be easily synthesized using a synthesizer.

When the target nucleic acid is a double-stranded DNA, a sequence complementary to either one of the sense strand and the antisense strand may be selected as the detection probe. In such cases, the sequence of the capture probe described above and the sequence of the detection probe are preferably sequences selected from the same strand.

The detection probe is not limited as long as the probe contains a sequence complementary to the target nucleic acid sequence, and any region may be selected therefor. The sequence preferably does not overlap with the sequence of the capture probe described above.

Homology between the base sequence of the detection probe and the base sequence of the capture probe is preferably low. The homology is preferably not more than 20%, more preferably not more than 10%. The homology between two base sequences herein means the value obtained by aligning the two sequences such that their bases match as much as possible (by insertion of a gap(s), if necessary) and then dividing the number of matched bases by the total number of bases (the larger number of bases, when the two base sequences have different numbers of bases). The homology can be easily calculated using commercially available software such as FASTA or BLAST (which is also available on the internet).

When a plurality of types of target nucleic acids contained in a sample nucleic acid is to be detected, a sequence which is 100% homologous among the target nucleic acids to be detected can be used as a common detection probe. When the homology of the common detection probe is not 100% among the target nucleic acids to be detected, a degenerate sequence may be used. The degenerate sequence may be selected by reference to "Biological Experiment Illustrated—Truly Productive PCR," (1999), ed., Hiroki Nakayama, published by Shujunsha Co., Ltd., pp. 121-125.

A label may be bound to the detection probe. When the detection probe is a nucleic acid, the label may be bound to either one or both of the 5'-end and the 3'-end. The label may also be introduced into the middle of the detection probe. The label may be bound by a chemical reaction, enzymatic reaction, or the like. The reaction is preferably a chemical reaction. More preferably, the label is bound to a terminus/termini during chemical synthesis of the detection probe. The label may also be bound in the middle of the detection probe. The label may be bound by a chemical reaction, and a biotin label may be inserted using a synthesizer. For example, a biotin label may be inserted using BiotinTEG Phosphoramidite, Biotin Phosphoramidite, or Biotin-dT, which is available from Glen Research Corporation, or the like.

For one type of target nucleic acid, one type of detection probe may be used, or a plurality of types of detection probes may be used at the same time. When a plurality of types of detection probes are used, the base sequences of the detection probes may be, of course, different from each other, and their lengths may be different from each other. To increase the S/N ratio in detection of the target nucleic acid, a plurality of types of detection probes are preferably used.

Examples of the label include known labeling substances such as protein-binding substances, fluorescent dyes, phosphorescent dyes, and radioisotopes. The label is preferably a protein-binding substance. Examples of the protein-binding substance include biotin. Biotin can bind to avidin or streptavidin. Avidin or streptavidin to which a fluorescent dye is bound, or to which an enzyme such as alkaline phosphatase or horse radish peroxidase is bound, may be used. When alkaline phosphatase or horse radish peroxidase is used, its substrate is added, and, as a result of the reaction between the substrate and the enzyme, luminescent reaction occurs. The luminescent reaction is detected using a plate reader, CCD camera or the like.

As the label, a fluorescent dye which can be simply measured and whose signal can be easily detected may be used. Specific examples of the fluorescent dye include known fluorescent dyes such as cyanine (cyanine 2), aminomethylcoumarin, fluorescein, indocarbocyanine (cyanine 3), cyanine 3.5, tetramethylrhodamine, rhodamine red, Texas red, indocarbocyanine (cyanine 5), cyanine 5.5, cyanine 7, Oyster, BODIPY dyes, and phycoerythrin. The fluorescent dye can be detected using a fluorescence microscope, fluorescence scanner or the like.

A luminescent semiconductor particle may be used as the label. Examples of the semiconductor particle include cadmium selenide (CdSe), cadmium telluride (CdTe), indium gallium phosphide (InGaP), chalcopyrite particles, and silicon (Si).

The detected signal is compared with the noise in the vicinity. More specifically, the signal value obtained for the position on the substrate where the capture probe is immobilized is compared with the signal value (noise value) obtained for a position on the substrate where the capture probe is not immobilized, to provide the ratio of the former value to the noise value as the S/N ratio.

Known examples of the method of immobilizing the capture probe on the support include methods in which an oligonucleic acid is synthesized on the upper surface of a support, and methods in which a preliminarily synthesized oligonucleic acid is dropped onto the upper surface of a support, and then immobilized. Any of these methods may be applied. Examples of the former methods include the method by Ronald et al. (U.S. Pat. No. 5,705,610), method by Michel et al. (U.S. Pat. No. 6,242,266), and method by Francesco et al. (U.S. Pat. No. 7,037,659). Since these methods use an organic solvent for DNA synthesis reaction, the material of the support is preferably resistant to organic solvents. For example, the glass support having an irregular structure prepared using the method described in Japanese Translated PCT Patent Application Laid-open No. 10-503841 may be used. Since, in particular, in the method by Francesco et al., light is radiated from the back side of the support to control synthesis of DNA, the material of the support preferably has translucency. Examples of the latter methods include the method by Hirota et al. (JP 3922454 B), and methods in which a glass capillary is used. Examples of the glass capillary include, but are not limited to, self-made glass capillaries and commercially available products such as a micropipette (manufactured by Microsupport Co., Ltd., MP-005).

Preparation of the DNA or RNA from living cells can be carried out by a known method, for example, the method by Blin et al. (Blin et al., Nucleic Acids Res. 3: 2303 (1976)) for DNA extraction, or the method by Favaloro et al. (Favaloro et. al., Methods Enzymol. 65: 718 (1980)) for RNA extraction. Examples of the nucleic acid to be immobilized also include linear and circular plasmid DNAs; chromosomal DNAs; DNA fragments prepared by cleaving these DNAs chemically or using a restriction enzyme; DNAs synthesized in vitro using an enzyme or the like; and chemically synthesized oligonucleotides.

The detection method is based on sandwich hybridization. Sandwich hybridization per se is well known. In this method, two different regions in the target nucleic acid are hybridized with a detection probe and a capture probe, respectively, to sandwich the target nucleic acid between the detection probe and the capture probe. The target nucleic acid is then quantified by quantifying the detection probe. The method has a step in which a complex formed by hybridization of the target nucleic acid with the detection probe and/or capture probe is irradiated with light to allow formation of a covalent bond(s) between a photoreactive group(s) in the detection probe and/or capture probe and a nucleic acid base(s) in the target nucleic acid. The light irradiation may be carried out with a light containing a wavelength that activates the photoreactive group employed. For example, when 3-cyanovinylcarbazole is used as the photoreactive group, a light having a wavelength of 340 to 380 nm may be used. Also, when the other photoreactive groups described above are used, a light having a wavelength of 340 to 380 nm may be used. The device to be used for the light irradiation may be a transilluminator, black light, UV-LED, UV laser, or the like that is capable of radiating a light containing the above-described wavelength.

Substitution of a nucleic acid base(s) with a photoreactive group(s) is carried out for either one of the detection probe and the capture probe, or for both of the detection probe and the capture probe. That is, as the method, any of the following methods may be employed: (A) a method comprising the step of forming a covalent bond(s) between only the detection probe and the target nucleic acid; (B) a method comprising the step of forming a covalent bond(s) between only the capture probe and the target nucleic acid; and (C) a method comprising the step of forming covalent bonds between the detection probe and the target nucleic acid, and between the capture probe and the target nucleic acid.

Examples of the method of detecting a nucleic acid include the methods (1) to (7) described below, which are different from each other in terms of the order of hybridization between the respective probes and the target nucleic acid, and selection of the probe to which the photoreactive group is introduced.

Method (1): The target nucleic acid is hybridized with a detection probe. Subsequently, the target nucleic acid hybridized with the detection probe is hybridized with a capture probe which is immobilized on a support and in which at least one nucleic acid base is substituted with a photoreactive group. The thus formed complex is irradiated with light to form a covalent bond(s) between the photoreactive group(s) in the capture probe and a nucleic acid base(s) in the target nucleic acid.

Method (2): The target nucleic acid is hybridized with a detection probe in which at least one nucleic acid base is substituted with a photoreactive group. The thus formed complex is irradiated with light to form a covalent bond(s) between the photoreactive group(s) in the detection probe and a nucleic acid base(s) in the target nucleic acid. The complex after the formation of the covalent bond(s) is hybridized with a capture probe immobilized on a support.

Method (3): The target nucleic acid is hybridized with a detection probe in which at least one nucleic acid base is substituted with a photoreactive group. The thus formed complex is irradiated with light to form a covalent bond(s) between the photoreactive group(s) in the detection probe and a nucleic acid base(s) in the target nucleic acid. The complex after formation of the covalent bond(s) is hybridized with a capture probe which is immobilized on a support and in which at least one nucleic acid base is substituted with a photoreactive group. The thus formed complex is irradiated with light to form a covalent bond(s) between the photoreactive group(s) in the capture probe and a nucleic acid base(s) in the target nucleic acid.

Method (4): The target nucleic acid is hybridized with a capture probe immobilized on a support. The formed complex is hybridized with a detection probe in which at least one nucleic acid base is substituted with a photoreactive group. The thus formed complex is irradiated with light to form a covalent bond(s) between the photoreactive group(s) in the detection probe and a nucleic acid base(s) in the target nucleic acid.

Method (5): The target nucleic acid is hybridized with a capture probe which is immobilized on a support and in which at least one nucleic acid base is substituted with a photoreactive group. The thus formed complex is irradiated with light to form a covalent bond(s) between the photoreactive group(s) in the capture probe and a nucleic acid base(s) in the target nucleic acid. The complex after the formation of the covalent bond(s) is hybridized with a detection probe.

Method (6): The target nucleic acid is hybridized with a capture probe which is immobilized on a support and in which at least one nucleic acid base is substituted with a photoreactive group. The thus formed complex is irradiated with light to form a covalent bond(s) between the photoreactive group(s) in the capture probe and a nucleic acid base(s) in the target nucleic acid. The complex after formation of the covalent bond(s) is hybridized with a detection probe in which at least one nucleic acid base is substituted with a photoreactive group. The thus formed complex is irradiated with light to form a covalent bond(s) between the photoreactive group(s) in the detection probe and a nucleic acid base(s) in the target nucleic acid.

Method (7): The target nucleic acid, a detection probe in which at least one nucleic acid base is substituted with a photoreactive group, and a capture probe which is immobilized on a support and in which at least one nucleic acid base is substituted with a photoreactive group are brought into contact with each other at the same time to allow hybridization of the detection probe and the capture probe with the target nucleic acid. The thus formed complex is irradiated with light to form a covalent bond(s) between the photoreactive group(s) in the detection probe and a nucleic acid base(s) in the target nucleic acid, and between the photoreactive group(s) in the capture probe and a nucleic acid base(s) in the target nucleic acid.

Among these methods, Methods (1) to (3) are preferred, and Methods (2) and (3) are more preferred.

The step of hybridizing the target nucleic acid with the capture probe and/or detection probe can be carried out in exactly the same manner as in conventional hybridization. The reaction temperature and time are appropriately selected depending on the chain length of the nucleic acid to be hybridized. In nucleic acid hybridization, the hybridization is usually carried out at about 30 to 70° C. for 1 minute to ten and several hours, and, in immune reaction, the reaction is usually carried out at about room temperature to 40° C. for 1 minute to several hours.

The amount of the detection probe used in each hybridization step is preferably small with respect to the amount of the target nucleic acid in view of reducing cross-hybridization of the detection probe. More specifically, the amount of the detection probe is preferably 1 to 10,000 equivalents (molar ratio), more preferably 1 to 1000 equivalents, still more preferably 1 to 100 equivalents, with respect to the amount of the target nucleic acid.

EXAMPLES

Our methods are described below in more detail by way of Examples. However, this disclosure is not limited to these Examples.

Preparation of Nucleic Acid

The nucleic acids used in the Examples and Comparative Examples below are shown in Table 1.

As target nucleic acids, a synthetic DNA "T-01," which has the base sequence of SEQ ID NO:1, a synthetic DNA "T-02," which has the base sequence of SEQ ID NO:2, and human genomic DNA were used. T-01 was synthesized by Japan Bio Services Co., Ltd. T-02 was synthesized by Japan Bio Services Co., Ltd.

Detection probes "D-01," "D-02," "D-05," "D-06," "D-09," "D-10," "D-11," and "D-12," which are synthetic DNAs each labeled with biotin at the 5'-end and the 3'-end (the 3'-end is Biotin-TEG labeled), were synthesized by Tsukuba Oligo Service Co., Ltd. D-01 is a synthetic DNA having the same base sequence as SEQ ID NO:3 except that the 23rd base, C, is replaced by a 3-cyanovinylcarbazole group as the photoreactive group. D-02 is a synthetic DNA having the same base sequence as SEQ ID NO:4 except that the 3rd base, A, is substituted with a 3-cyanovinylcarbazole group as the photoreactive group. D-05 is a synthetic DNA having the same base sequence as SEQ ID NO:5 except that the 13th base, T, is substituted with a 3-cyanovinylcarbazole group as the photoreactive group. D-06 is a synthetic DNA having the same base sequence as SEQ ID NO:6 except that the 13th base, T, is substituted with a 3-cyanovinylcarbazole group as the photoreactive group. D-09 is a synthetic DNA having the same base sequence as SEQ ID NO:7 except that the 22nd base, A, is substituted with a 3-cyanovinylcarbazole group as the photoreactive group. D-10 is a synthetic DNA having the same base sequence as SEQ ID NO:8 except that the 23rd base, T, is substituted with a 3-cyanovinylcarbazole group as the photoreactive group. D-11 is a synthetic DNA having the same base sequence as SEQ ID NO:9 except that the 16th base, C, is substituted with a 3-cyanovinylcarbazole group as the photoreactive group. D-12 is a synthetic DNA having the same base sequence as SEQ ID NO:10 except that the 21st base, T, is substituted with a 3-cyanovinylcarbazole group as the photoreactive group.

Detection probes "D-03," "D-04," "D-07," "D-08," "D-13," "D-14," "D-15," and "D-16" are synthetic DNAs having the base sequences of SEQ ID NOs:3, 4, 5, 6, 7, 8, 9, and 10, respectively, and each of the probes is labeled with biotin at the 5'-end and the 3'-end (the 3'-end is Biotin-TEG labeled). These probes were synthesized by Operon Biotechnologies.

A capture probe "C-01" is a synthetic DNA having the base sequence of SEQ ID NO:11, and having amino modification introduced at the 5'-end. This probe was synthesized by Operon Biotechnologies.

A capture probe "C-02" is a synthetic DNA having the same base sequence as SEQ ID NO:12 except that the 18th base, T, is substituted with a 3-cyanovinylcarbazole group as the photoreactive group, which synthetic DNA is labeled with biotin at the 5'-end. This probe was synthesized by Tsukuba Oligo Service Co., Ltd.

A capture probe "C-03" is a synthetic DNA having the base sequence of SEQ ID NO:12 whose 5'-end is labeled with biotin. This probe was synthesized by Operon Biotechnologies.

A capture probe "C-04" is a PNA (Peptide Nucleic Acid) in which the N'-terminus is labeled with biotin via two molecules of O linkers (—NH(CH$_2$CH$_2$O)$_2$CH$_2$CO—), and the C'-terminus is modified with lysine. This probe was synthesized by PANAGENE.

A capture probe "C-05" is a synthetic DNA having the same base sequence as SEQ ID N0:13 except that the 19th base, A, is substituted with a 3-cyanovinylcarbazole group as the photoreactive group, and having amino modification introduced at the 5'-end. This probe was synthesized by Tsukuba Oligo Service Co., Ltd.

Capture probes "C-06," "C-07," "C-08," "C-09," and "C-10" are synthetic DNAs having the base sequences of SEQ ID NOs:13, 14, 15, 16, and 17, respectively, and each of the probes has amino modification introduced at the 5'-end. These probes were synthesized by Operon Biotechnologies.

TABLE 1

| Type of nucleic acid | Name | Base sequence | SEQ ID NO: | Note |
|---|---|---|---|---|
| Target nucleic acid | T-01 | 5'-GAAAAATAAACTGTAAATCATATTCC TCCCCATGTCGTAGGTACTCCTTAAAGTTA GTATTTTTATATGTAGTTTCTGAAGTAGAT ATGGCAGCACATAATGACATATTTGTACT GCGTGTAGTATCAACAACAGTAACAAA-3' | 1 | |
| | T-02 | 5'-TCAGAGGTAACCATAGAACCACTAGG TGTAGGAAAATAATTTGAACTGGCTAAAT TTGCAGTAGACCCAGAGCCTTTAATGTAT AAATCGTCTGGTACATTTTCACCAACAGT ACCAGCCCTATTAAATAAATGTCTAAC-3' | 2 | |
| Detection probe | D-01 | 5'-TTTGTTACTGTTGTTGATACTAK-3' | 18 | Biotinylation at the 5'-end and the 3'-end |
| | D-02 | 5'-GAKTATGATTTACAGTTTATTTTTC-3' | 19 | Biotinylation at the 5'-end and the 3'-end |
| | D-03 | 5'-TTTGTTACTGTTGTTGATACTAC-3' | 3 | Biotinylation at the 5'-end and the 3'-end |
| | D-04 | 5'-GAATATGATTTACAGTTTATTTTTC-3' | 4 | Biotinylation at the 5'-end and the 3'-end |
| | D-05 | 5'-ACATTTATTTAAKAGGGCTGGTACT-3' | 20 | Biotinylation at the 5'-end and the 3'-end |
| | D-06 | 5'-CTAGTGGTTCTAKGGTTACCTCTGA-3' | 21 | Biotinylation at the 5'-end and the 3'-end |
| | D-07 | 5'-ACATTTATTTAATAGGGCTGGTACT-3' | 5 | Biotinylation at the 5'-end and the 3'-end |
| | D-08 | 5'-CTAGTGGTTCTATGGTTACCTCTGA-3' | 6 | Biotinylation at the 5'-end and the 3'-end |
| | D-09 | 5'-ACATGTCACACATAAGGTTAAKAC ACTATCAAATACTCCA-3' | 22 | Biotinylation at the 5'-end and the 3'-end |
| | D-10 | 5'-CAGTCATTTTCAGCAGGCCTTAKAA TAAAAATAATGAAAA-3' | 23 | Biotinylation at the 5'-end and the 3'-end |
| | D-11 | 5'-GATCATATTCGTCCAKAAAATGAT TCTGAATTAGCTGTAT-3' | 24 | Biotinylation at the 5'-end and the 3'-end |
| | D-12 | 5'-GAATGGTCCTGCACCAGTAAKATG CATATTAAAACAAGAT-3' | 25 | Biotinylation at the 5'-end and the 3'-end |
| | D-13 | 5'-ACATGTCACACATAAGGTTAAAAC ACTATCAAATACTCCA-3' | 7 | Biotinylation at the 5'-end and the 3'-end |
| | D-14 | 5'-CAGTCATTTTCAGCAGGCCTTATAA TAAAAATAATGAAAA-3' | 8 | Biotinylation at the 5'-end and the 3'-end |
| | D-15 | 5'-GATCATATTCGTCCACAAAATGATTC TGAATTAGCTGTAT-3' | 9 | Biotinylation at the 5'-end and the 3'-end |
| | D-16 | 5'-GAATGGTCCTGCACCAGTAATATG CATATTAAAACAAGAT-3' | 10 | Biotinylation at the 5'-end and the 3'-end |
| Capture probe | C-01 | 5'-GTCATTATGTGCTGCCATATCTACTTCAGA-3' | 11 | Amination at the 5'-end |
| | C-02 | 5'-GTCATTATGTGCTGCCAKATCTACTTCAGA-3' | 26 | Biotinylation at the 5'-end |
| | C-03 | 5'-GTCATTATGTGCTGCCATATCTACTTCAGA-3' | 12 | Biotinylation at the 5'-end |
| | C-04 | N'-TGTGCTGCCATATCTA-C' | 27 | PNA; Biotinylation at the N'-terminus, Lysine modification at the C'-terminus |

TABLE 1-continued

| Type of nucleic acid | Name | Base sequence | SEQ ID NO: | Note |
|---|---|---|---|---|
| | C-05 | 5'-TTTTTGATTTATACATTAKAGGCTCTGGGTCTACT-3' | 28 | Amination at the 5'-end |
| | C-06 | 5'-TTTTTGATTTATACATTAAAGGCTCTGGGTCTACT-3' | 13 | Amination at the 5'-end |
| | C-07 | 5'-AGTTGGAGCTGGTGGCGTAGG-3' | 14 | Amination at the 5'-end |
| | C-08 | 5'-AGTTGGAGCTAGTGGCGTAGG-3' | 15 | Amination at the 5'-end |
| | C-09 | 5'-AGTTGGAGCTCGTGGCGTAGG-3' | 16 | Amination at the 5'-end |
| | C-10 | 5'-AGTTGGAGCTTGTGGCGTAGG-3' | 17 | Amination at the 5'-end |

In Table 1, each "K" in the base sequences represents a 3-cyanovinylcarbazole group introduced as the photoreactive group. In C-04, the N'-terminus and the C'-terminus mean the amino-terminal side and the carboxyl-terminal side of the PNA, respectively.

Example 1

In Example 1, the target nucleic acid T-01 was hybridized with the detection probes D-01 and D-02, in each of which the photoreactive group is introduced. The complex formed was irradiated with light to allow formation of a covalent bond between each detection probe and the target nucleic acid, and the complex was then hybridized with the capture probe C-01, followed by detection of the target nucleic acid.
Preparation of DNA Chip
To a substrate of "3D-Gene" (registered trademark), manufactured by Toray Industries, Inc. (256-column substrate), C-01 was immobilized as the capture probe.
Hybridization and Detection
T-01 (10 µM), D-01 (100 µM), and D-02 (100 µM) were mixed together such that the amount of each of D-01 and D-02 used was 1 molar equivalent with respect to T-01, and the resulting mixture was diluted with 10 mM phosphate buffer (supplemented with 100 mM sodium chloride). Solutions with 3 different molar concentrations, that is, 0.1, 1, and 100 amol (total volume, 5 µL each), were prepared from the obtained solution, and each solution was subjected to the following operations.
The mixture solutions were kept on a heat block at 95° C. for 5 minutes, and then slowly cooled to room temperature. The solutions were then transferred to glass tubes, and irradiated with light having a wavelength of 365 nm ($10 \mu W/cm^2$) using a transilluminator for 20 minutes. To each of these solutions, 35 µL of 1×hybridization solution (1 wt % BSA (bovine serum albumin), 5×SSC, 1 wt % SDS (sodium dodecyl sulfate), 50 ng/ml salmon sperm DNA solution, 5 wt % dextran sulfate sodium, 30% formamide) was added to provide a hybridization solution. The whole hybridization solution was injected to the DNA chip, and the DNA chip was then placed in an incubator warmed at 32° C. Hybridization was carried out according to the standard protocol for "3D-Gene" with stirring by rotation at 250 rpm at 32° C. for 2 hours. Thereafter, the DNA chip was washed for 5 minutes with a washing liquid (0.5×SSC, 0.1 wt % SDS (sodium dodecyl sulfate)) warmed at 30° C., and then dried using a spin drier (Wakenyaku Co., Ltd.). A solution prepared by adding streptavidin-phycoerythrin (ProZyme, Inc.) to a staining solution (50 ng/µl streptavidin-phycoerythrin, 100 mM MES, 1 M NaCl, 0.05 wt % Tween 20, 2 mg/ml BSA (bovine serum albumin)) was added dropwise onto the DNA chip. This was followed by incubation at 35° C. for 5 minutes. The DNA chip was then washed for 5 minutes with a washing liquid (6×SSPE, 0.01 wt % Tween 20) warmed at 30° C., and dried using a spin drier (Wakenyaku Co., Ltd.). The stained DNA chip was subjected to detection of fluorescent signals using a DNA chip scanner (Toray Industries, Inc.). The scanner was set as follows: laser output, 100%; photomultiplier voltage, 70%.

Detection results for the target nucleic acid T-01 are shown in Table 2. Each number in Table 2 indicates the S/N ratio. The S/N ratio was calculated as the ratio of the signal value detected at a position on the substrate where the capture probe was immobilized to the signal value detected at a position on the substrate where the capture probe was not immobilized. An S/N ratio of not more than 1 indicates that the target nucleic acid could not be detected.

By formation of covalent bonds between the target nucleic acid and the detection probes by irradiation of light, the target nucleic acid could be detected at each of concentrations of 0.1, 1, and 100 amol even though the amount of each detection probe relative to the target nucleic acid, 1 molar equivalent, was much smaller than in conventional methods.

Comparative Example 1

The same operations as in Example 1 were carried out except that D-03 and D-04 were used instead of D-01 and D-02, respectively, as the detection probes, and the step of forming covalent bonds between the detection probes and the target nucleic acid by light irradiation of the complex formed by hybridization was not carried out. A mixture of the target nucleic acid T-01 and 1 molar equivalent each of D-03 and D-04 with respect to T-01 was prepared, and used for detection of the target nucleic acid T-01.

Similarly, a mixture of the target nucleic acid T-01 and 1000 molar equivalents each of D-03 and D-04 with respect to T-01 was prepared, and used for detection of the target nucleic acid T-01.

The results are shown in Table 2.
In Comparative Example 1, use of the detection probe at 1 molar equivalent resulted in a large decrease in the S/N ratio relative to Example 1, and T-01 at a concentration of 1 amol could not be detected. Also, when the amount of the detection probe was increased to 1000 molar equivalents, the S/N ratio largely decreased relative to Example 1, and T-01 at a concentration of 0.1 amol could not be detected.

TABLE 2

| | S/N ratio of target nucleic acid at each concentration | | |
|---|---|---|---|
| | 100 amol | 1 amol | 0.1 amol |
| Example 1 | 87.8 | 5.8 | 2.1 |
| Comparative Example 1 (Detection probe, 1 equivalent) | 4.2 | 1.0 | 1.0 |
| Comparative Example 1 (Detection probe, 1000 equivalents) | 19.8 | 1.1 | 1.0 |

From the results of Example 1 and Comparative Example 1 described above, we found that, by sandwich hybridization in which a complex formed by hybridization between a target nucleic acid and photoreactive-group-containing detection probes is irradiated with light to allow formation of covalent bonds between the detection probes and the target nucleic acid, a small amount of the target nucleic acid can be detected even with smaller amounts of the detection probes, and the target nucleic acid can be detected with high sensitivity.

Example 2

In Example 2, the target nucleic acid T-01 was hybridized with the detection probes D-03 and D-04 to form a complex, and the complex was then hybridized with the capture probe C-02, in which the photoreactive group is introduced. The complex formed was irradiated with light to allow formation of a covalent bond between the capture probe and the target nucleic acid, and the target nucleic acid was then detected.

Preparation of Capture-Probe-Immobilized Beads

On avidin-coated beads (manufactured by Thermo Fisher Scientific, Inc.), C-02 was immobilized as a capture probe, and the resulting beads were subjected to blocking treatment using an aqueous biotin solution.

Hybridization and Detection

T-01 (10 µM) and, as detection probes, D-03 (100 µM) and D-04 (100 µM) were mixed together such that the amount of each of D-03 and D-04 used was 1 molar equivalent with respect to T-01, and the resulting mixture was diluted with 10 mM phosphate buffer (supplemented with 100 mM sodium chloride) to provide a mixture solution with a total volume of 200 µL, containing T-01 at a final concentration of 0.25 µM. This mixture solution was kept on a heat block at 95° C. for 5 minutes, and then slowly cooled to room temperature. In an "OMNIFIT" (registered trademark of ISIS Co., Ltd.) glass column (inner diameter, 3 mm; provided with 2-µm stainless frits at both ends as column stoppers), beads on which C-02 is immobilized were placed, and the above mixture solution (200 µL) was added thereto, followed by irradiating the resulting mixture with black light at 365 nm with stirring for 5 minutes. The solution was then removed by filtration, and the beads were washed with 50% aqueous DMSO solution, followed by adding an aqueous solution of Cy3-streptavidin (0.01 µM) thereto to perform staining. The solution was then removed by filtration, and the beads were washed with 50% aqueous DMSO solution. The stained beads were detected using a fluorescence microscope (manufactured by Olympus Corporation) equipped with a CCD camera. The results are shown in Table 3.

Example 3

In Example 3, the target nucleic acid T-01 was hybridized with the detection probes D-01 and D-02, in each of which the photoreactive group is introduced. The complex formed was irradiated with light to allow formation of a covalent bond between each detection probe and the target nucleic acid, and the complex was then hybridized with the capture probe C-03, followed by detection of the target nucleic acid.

Preparation of Capture-Probe-Immobilized Beads

On avidin-coated beads (manufactured by Thermo Fisher Scientific, Inc.), C-03 was immobilized, and the resulting beads were subjected to blocking treatment using an aqueous biotin solution.

Hybridization and Detection

T-01 (10 µM), D-01 (100 µM) and D-02 (100 µM) were mixed together such that the amount of each of D-01 and D-02 used was 1 molar equivalent with respect to T-01, and the resulting mixture was diluted with 10 mM phosphate buffer (supplemented with 100 mM sodium chloride) to provide a mixture solution with a total volume of 400 µL containing T-01 at a final concentration of 0.25 µM. This mixture solution was kept on a heat block at 95° C. for 5 minutes, and then slowly cooled to room temperature. The resulting mixture was transferred to a glass tube, and irradiated with light having a wavelength of 365 nm (10 µW/cm$^2$) using a transilluminator for 20 minutes. In an "OMNIFIT" glass column (inner diameter, 3 mm; provided with 2-µm stainless frits at both ends as column stoppers), beads on which C-03 is immobilized were placed, and the above mixture solution (200 µL) was added thereto, followed by stirring the resulting mixture for 5 minutes. The solution was then removed by filtration, and the beads were washed with 50% aqueous DMSO solution, followed by adding an aqueous solution of Cy3-streptavidin (0.01 µM) thereto to perform staining. The solution was then removed by filtration, and the beads were washed with 50% aqueous DMSO solution. The stained beads were detected using a fluorescence microscope (manufactured by Olympus Corporation). The results are shown in Table 3.

Example 4

The same operations as in Example 3 were carried out except that C-04 was used instead of C-03 as the capture probe, and the target nucleic acid T-01 was detected. The results are shown in Table 3.

Example 5

In Example 5, the target nucleic acid T-01 was hybridized with the detection probes D-01 and D-02, in each of which the photoreactive group is introduced. The complex formed was irradiated with light to allow formation of a covalent bond between each detection probe and the target nucleic acid, and the complex was further hybridized with the capture probe C-02, in which the photoreactive group is introduced. The complex formed was irradiated with light to allow formation of a covalent bond between the capture probe and the target nucleic acid, and the target nucleic acid was then detected.

Preparation of Capture-Probe-Immobilized Beads

On avidin-coated beads (manufactured by Thermo Fisher Scientific, Inc.), C-02 was immobilized as a capture probe, and the resulting beads were subjected to blocking treatment using an aqueous biotin solution.

Hybridization and Detection

T-01 (10 µM), D-01 (100 µM) and D-02 (100 µM) were mixed together such that the amount of each of D-01 and D-02 used was 1 molar equivalent with respect to T-01, and the resulting mixture was diluted with 10 mM phosphate buffer (supplemented with 100 mM sodium chloride) to provide a mixture solution with a total volume of 200 µL containing T-01 at a final concentration of 0.25 µM. This mixture solution was kept on a heat block at 95° C. for 5 minutes, and then slowly cooled to room temperature. The resulting mixture was transferred to a glass tube, and irradiated with light having a wavelength of 365 nm (10 µW/cm$^2$) using a transilluminator for 20 minutes. In an "OMNIFIT" glass column (inner diameter, 3 mm; provided with 2-µm stainless frits at both ends as column stoppers), beads on which C-02 is immobilized were placed, and the above mixture solution (200 µL) was added thereto, followed by irradiating the resulting mixture with black light at 365 nm with stirring for 5 minutes. The solution was then removed by filtration, and the beads were washed with 50% aqueous DMSO solution, followed by adding an aqueous solution of Cy3-streptavidin (0.01 µM) thereto to perform staining. The solution was then removed by filtration, and the beads were washed with 50% aqueous DMSO solution. The stained beads were detected using a fluorescence microscope (manufactured by Olympus Corporation). The results are shown in Table 3.

Comparative Example 2

The same operations as in Example 2 were carried out except that C-03 was used instead of C-02 as the capture probe, and that the step of forming a covalent bond between the capture probe and the target nucleic acid by light irradiation of the complex formed by hybridization was not carried out. A mixture of the target nucleic acid T-01 and 1 molar equivalent each of D-03 and D-04 with respect to T-01 was prepared, and used for detection of the target nucleic acid T-01.

Similarly, a mixture of the target nucleic acid T-01 and 100 molar equivalents each of D-03 and D-04 with respect to T-01 was prepared, and used for detection of the target nucleic acid T-01. The results are shown in Table 3.

TABLE 3

| | Detection probe | Photocrosslinking between detection probe and target nucleic acid | Capture probe | Photocrosslinking between capture probe and target nucleic acid | S/N ratio |
|---|---|---|---|---|---|
| Example 2 | D-03, D-04 | No | C-02 | Yes | 38.3 |
| Example 3 | D-01, D-02 | Yes | C-03 | No | 72.9 |
| Example 4 | D-01, D-02 | Yes | C-04 | No | 154.5 |
| Example 5 | D-01, D-02 | Yes | C-02 | Yes | 208.0 |
| Comparative Example 2 (Detection probe, 1 equivalent) | D-03, D-04 | No | C-03 | No | 17.3 |
| Comparative Example 2 (Detection probe, 100 equivalents) | D-03, D-04 | No | C-03 | No | 19.4 |

In any of Examples 2 to 5, by formation of a covalent bond(s) between the detection probes and/or capture probe and the target nucleic acid, the target nucleic acid at a concentration of 0.05 nmol could be detected with high sensitivity even though the amount of each detection probe relative to the target nucleic acid was 1 molar equivalent. We also found that the target nucleic acid can be detected with high sensitivity in any of the following cases: formation of a covalent bond only between each detection probe and the target nucleic acid; formation of a covalent bond only between the capture probe and the target nucleic acid; and formation of covalent bonds both between each detection probe and the target nucleic acid and between the capture probe and the target nucleic acid. Detection sensitivity was especially high when covalent bonds were formed both for each detection probe and the capture probe. We also found that not only a nucleic acid, but also a peptide nucleic acid can be used as the probe.

On the other hand, in Comparative Example 2, use of the detection probe at 1 molar equivalent resulted in a large decrease in the S/N ratio relative to the Examples. Also, when the detection probe was used in an amount of 100 molar equivalents, the S/N ratio was considerably lower than in the Examples, and detection sensitivity could not be improved even by the use of a larger amount of the detection probe.

Thus, we found that, by sandwich hybridization in which a complex formed by hybridization between a target nucleic acid and detection probes and/or capture probes containing photoreactive groups introduced therein is irradiated with light to allow formation of covalent bonds between the detection probes and/or capture probes and the target nucleic acid, a small amount of the target nucleic acid can be detected with high sensitivity even with smaller amounts of the detection probes.

Example 6

The same operations as in Example 1 were carried out except that T-02 was used instead of T-01 as the target nucleic acid; D-05 and D-06 were used instead of D-01 and D-02 as the detection probes; C-05 was used instead of C-01 as the capture probe; and T-02 (1004), D-05 (100 µM), and D-06 (100 µM) were mixed together such that the amount of each of D-05 and D-06 used was 1 molar equivalent with respect to T-02, and the resulting mixture was diluted with 10 mM phosphate buffer (supplemented with 100 mM sodium chloride) to provide solutions with two different molar concentrations, 0.1 and 0.01 amol, followed by performing hybridization on the DNA chip and then irradiation of the resulting DNA chip with black light at 365 nm for 5 minutes, thereby detecting the target nucleic acid T-02. The results are shown in Table 4.

By formation of covalent bonds between the target nucleic acid and the detection probes and between the target nucleic acid and the capture probe by light irradiation, the target nucleic acid at a concentration of either 0.1 or 0.01 amol could be detected even though the amount of each detection probe relative to the target nucleic acid, 1 molar equivalent, was much smaller than in conventional methods.

Comparative Example 3

The same operations as in Example 6 were carried out except that D-07 and D-08 were used instead of D-05 and D-06 as the detection probes; C-06 was used instead of C-05 as the capture probe; the step of forming covalent bonds between the detection probes and the target nucleic acid by light irradiation of the complex formed by hybridization was not carried out; and the step of irradiating, after the hybridization on the DNA chip, the DNA chip with light to form a covalent bond between the capture probe and the target nucleic acid was not carried out; thereby detecting the target nucleic acid T-02.

Similarly, a mixture of the target nucleic acid T-02 and 100,000 molar equivalents each of D-07 and D-08 with respect to T-02 was prepared, and used for detection of the target nucleic acid T-02. The results are shown in Table 4.

In Comparative Example 3, not only when 1 molar equivalent of the detection probe was used, but also when 100,000 molar equivalents of the detection probe was used, the S/N ratio was much lower than in Example 6, and T-02 could not be detected.

TABLE 4

|  | S/N ratio of target nucleic acid at each concentration | |
| --- | --- | --- |
|  | 0.1 amol | 0.01 amol |
| Example 6 | 4.2 | 1.9 |
| Comparative Example 3 (Detection probe, 1 equivalent) | 1.0 | 1.0 |
| Comparative Example 3 (Detection probe, 100,000 equivalents) | 1.0 | 1.0 |

From the results of Example 6 and Comparative Example 3 described above, we found that, by sandwich hybridization in which a complex formed by hybridization between a target nucleic acid and photoreactive-group-containing detection probes is irradiated with light to allow formation of covalent bonds between the detection probes and the target nucleic acid, and a complex formed by hybridization between the target nucleic acid and a photoreactive-group-containing capture probe on a DNA chip is irradiated with light to allow formation of a covalent bond between the capture probe and the target nucleic acid, a small amount of the target nucleic acid can be detected with high sensitivity even with smaller amounts of the detection probes.

Example 7

Application of our methods to detect SNPs (single nucleotide polymorphisms) was studied. Since human genomic DNA is used in the Example, the target nucleic acid is double-stranded nucleic acid.
Preparation of DNA Chip To a substrate of "3D-Gene" (registered trademark), manufactured by Toray Industries, Inc. (256-column substrate), the capture probes C-07 (wild type), C-08 (Gly12Ser variant), C-09 (Gly12Arg variant), and C-10 (Gly12Cys variant) shown in Table 1 were immobilized.
Preparation of Sample DNA As a sample DNA, DNA extracted from A549 cells was used. A549 cells are cultured cells derived from a lung cancer tissue, and known to have the Gly12Ser mutation. Fragmentation of 5 µg of genomic DNA extracted from A549 cells was carried out by ultrasonication (Covaris s220), and 600 ng of the fragmented genomic DNA was used for detection. The fragmentation treatment was carried out according to the method recommended by the manufacturer. The lengths of the fragments were evaluated using a Bioanalyzer (manufactured by Agilent Technologies, Inc.). It is known that 2 pg of DNA is contained in each cell. Since each gene for SNPs has two copies in each cell, 1 amol of sequences of genes for SNPs are contained in 600 ng of genomic DNA.
Hybridization and Detection A sample DNA was prepared such that the amount of each of the detection probes D-09, D-10, D-11, and D-12 used for 600 ng (1 amol) of genomic DNA was 100 molar equivalents (that is, the amount of each detection probe was 100 amol) (total volume, 5 µL, each), and subjected to the following operations.

The mixture solutions were kept on a heat block at 95° C. for 5 minutes, and then slowly cooled to room temperature. The solutions were then transferred to glass tubes, and irradiated with light having a wavelength of 365 nm (10 µW/cm$^2$) using a transilluminator for 20 minutes. To each of these solutions, 35 µL of 1×hybridization solution (1 wt % BSA (bovine serum albumin), 5×SSC, 1 wt % SDS (sodium dodecyl sulfate), 50 ng/ml salmon sperm DNA solution, 5 wt % dextran sulfate sodium, 30% formamide) was added to provide a hybridization solution. The whole hybridization solution was injected to the DNA chip, and the DNA chip was then placed in an incubator warmed at 32° C. Hybridization was carried out according to the standard protocol for "3D-Gene" with stirring by rotation at 250 rpm at 32° C. for 2 hours. Thereafter, the DNA chip was washed for 5 minutes with a washing liquid (0.5×SSC, 0.1 wt % SDS (sodium dodecyl sulfate)) warmed at 30° C., and then dried using a spin drier (Wakenyaku Co., Ltd.). A solution prepared by adding streptavidin-phycoerythrin (ProZyme, Inc.) to a staining solution (50 ng/µl streptavidin-phycoerythrin, 100 mM MES, 1 M NaCl, 0.05 wt % Tween 20, 2 mg/ml BSA (bovine serum albumin)) was added dropwise onto the DNA chip. This was followed by incubation at 35° C. for 5 minutes. The DNA chip was then washed for 5 minutes with a washing liquid (6×SSPE, 0.01 wt % Tween 20) warmed at 30° C., and dried using a spin drier (Wakenyaku Co., Ltd.). The stained DNA chip was subjected to detection of fluorescent signals using a DNA chip scanner (Toray Industries, Inc.). The scanner was set as follows: laser output, 100%; photomultiplier voltage, 70%.

The detection results of the target nucleic acid are shown in Table 5. The capture probe "C-08," having the Gly12Ser mutation, showed the highest S/N ratio. A549 cells are known to have the Gly12Ser mutation, and the detection results were consistent with this fact.

By formation of covalent bonds between the target nucleic acid and the detection probes by light irradiation, the genomic DNA, which is double-stranded nucleic acid, could be detected and the SNPs could be correctly detected even though the amount of each detection probe relative to the target nucleic acid, 100 molar equivalents, was much smaller than in conventional methods.

Comparative Example 4

The same operations as in Example 7 were carried out except that D-13, D-14, D-15, and D-16 were used instead of D-09, D-10, D-11, and D-12 as the detection probes, and that the step of forming covalent bonds between the detection probes and the target nucleic acid by light irradiation of the complex formed by hybridization was not carried out, to detect the target nucleic acid.

Similarly, a mixture of the target nucleic acid and 100,000 molar equivalents each of D-13, D-14, D-15, and D-16 with respect to the target nucleic acid was prepared, and used for detection of the target nucleic acid. The results are shown in Table 5.

In Comparative Example 4, when each detection probe was used at 100 molar equivalents, the wild-type capture probe C-07 showed the highest S/N ratio, and the Gly12Ser mutation could not be detected at all. Even when each detection probe was used at 100,000 molar equivalents, the S/N ratios were much lower than in Example 7, and the Gly12Ser mutation could not be detected.

TABLE 5

| | S/N ratio of each variant capture probe | | | |
|---|---|---|---|---|
| | C-07 (wild type) | C-08 (Gly12Ser variant) | C-09 (Gly12Arg variant) | C-10 (Gly12Cys variant) |
| Example 7 | 1.0 | 3.1 | 1.1 | 1.0 |
| Comparative Example 4 (Detection probe, 100 equivalents) | 1.2 | 1.0 | 1.1 | 1.0 |
| Comparative Example 4 (Detection probe, 100,000 equivalents) | 1.3 | 1.1 | 1.1 | 1.1 |

SEQUENCE LISTING FREE TEXT

SEQ ID NO:1 Synthetic DNA
SEQ ID NO:2 Synthetic DNA
SEQ ID NO:3 Synthetic DNA (biotinylation at the 5'-end and the 3'-end)
SEQ ID NO:4 Synthetic DNA (biotinylation at the 5'-end and the 3'-end)
SEQ ID NO:5 Synthetic DNA (biotinylation at the 5'-end and the 3'-end)
SEQ ID NO:6 Synthetic DNA (biotinylation at the 5'-end and the 3'-end)
SEQ ID NO:7 Synthetic DNA (biotinylation at the 5'-end and the 3'-end)
SEQ ID NO:8 Synthetic DNA (biotinylation at the 5'-end and the 3'-end)
SEQ ID NO:9 Synthetic DNA (biotinylation at the 5'-end and the 3'-end)
SEQ ID NO:10 Synthetic DNA (biotinylation at the 5'-end and the 3'-end)
SEQ ID NO:11 Synthetic DNA (amination at the 5'-end)
SEQ ID NO:12 Synthetic DNA (biotinylation at the 5'-end)
SEQ ID NO:13 Synthetic DNA (amination at the 5'-end)
SEQ ID NO:14 Synthetic DNA (amination at the 5'-end)
SEQ ID NO:15 Synthetic DNA (amination at the 5'-end)
SEQ ID NO:16 Synthetic DNA (amination at the 5'-end)
SEQ ID NO:17 Synthetic DNA (amination at the 5'-end)

The invention claimed is:

1. A method of detecting a target nucleic acid by sandwich hybridization using a detection probe that hybridizes with the target nucleic acid, and a capture probe immobilized on a support wherein at least one nucleic acid base in the nucleic acid molecule(s) of the detection probe and at least one nucleic acid base in the nucleic acid molecule(s) of the capture probe is substituted with a photoreactive group, comprising:

irradiating, with light, a complex formed by hybridization between the target nucleic acid and the detection probe and/or capture probe to allow formation of a covalent bond(s) between the photoreactive group(s) and a nucleic acid base(s) in the target nucleic acid, wherein the amount of the detection probe is 1 to 10,000 equivalents (molar ratio) with respect to the amount of the target nucleic acid.

2. The method according to claim 1, wherein the photoreactive group is at least one selected from the group consisting of 3-cyanovinylcarbazole, p-carbamoylvinylphenol, 4,5',8-trimethylpsoralen, and N3-methyl-5-cyanovinyluracil.

* * * * *